US006429327B1

(12) United States Patent
Sims et al.

(10) Patent No.: US 6,429,327 B1
(45) Date of Patent: Aug. 6, 2002

(54) ORGANOMETALLIC CATALYSTS

(75) Inventors: Philip Franklin Sims, Cherryville; James Anthony Schwindeman, Lincolnton, both of NC (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/487,420

(22) Filed: Jan. 20, 2000

Related U.S. Application Data

(60) Provisional application No. 60/116,722, filed on Jan. 21, 1999.

(51) Int. Cl.$^7$ .................................................. C07F 7/08
(52) U.S. Cl. ....................... 556/480; 502/103; 502/117; 502/225
(58) Field of Search ............................ 556/480; 502/103, 502/117, 225

(56) References Cited

U.S. PATENT DOCUMENTS

| | | | |
|---|---|---|---|
| 4,593,112 A | | 6/1986 | Takamizawa et al. |
| 4,642,374 A | * | 2/1987 | Lucy et al. ............ 502/225 X |
| 4,650,891 A | * | 3/1987 | Lennon ..................... 556/480 |
| 5,068,386 A | * | 11/1991 | Shirahata .................. 556/480 |
| 5,312,949 A | | 5/1994 | Shirahata |
| 5,332,853 A | | 7/1994 | Morrison et al. |
| 5,872,274 A | * | 2/1999 | Cannady et al. ............ 556/480 |
| 6,156,918 A | * | 12/2000 | Winterfeld et al. ......... 556/480 |

FOREIGN PATENT DOCUMENTS

| | | |
|---|---|---|
| EP | 0 278 368 A1 | 8/1988 |
| EP | 0 298 487 A2 | 1/1989 |
| EP | 0 405 560 A2 | 1/1991 |
| EP | 0 556 802 A1 | 8/1993 |
| EP | 0 557 762 A1 | 9/1993 |
| EP | 0 652 221 A1 | 5/1995 |
| EP | 0 656 363 A1 | 6/1995 |

OTHER PUBLICATIONS

Japanese Patent Abstract 62022790 (1987).
Japanese Patent Abstract 60222492 (1985).
Japanese Patent Abstract 8291180 (1996).
Japanese Patent Abstract 8119978 (1996).
Japanese Patent Abstract 6247987 (1994).
Japanese Patent Abstract 6128274 (1994).
Japanese Patent Abstract 8311083 (1996).
Japanese Patent Abstract 8333374 (1996).
P. Lennon et al., *Organometallics*, 1989, 8, 1122–1123.
R. Corriu et al., *Organometallics*, 1988, 7, 237–238.
H.O. House et al., *J. Org. Chem.*, 1966, 31, 3128–3141.

* cited by examiner

*Primary Examiner*—Paul F. Shaver
(74) *Attorney, Agent, or Firm*—Myers, Bigel, Sibley and Sajovec, PA

(57) ABSTRACT

Processes for the synthesis of substituted silanes from alkyl magnesium compounds using a mixture of catalysts. The catalyst systems include both a copper halide and a salt of a Group IA, IIA, IIA, or IVA element or a transition metal.

45 Claims, No Drawings

ORGANOMETALLIC CATALYSTS

CROSS REFERENCE TO RELATED APPLICATIONS

This application is related to commonly owned copending provisional application Ser. No. 60/116,722, filed Jan. 21, 1999, and claims the benefit thereof under 35 USC Section 119(e).

FIELD OF THE INVENTION

This invention relates to catalyst systems and processes of using the same, and more particularly to catalyst systems for making alkyl substituted compounds.

BACKGROUND OF THE INVENTION

In the synthesis of organic compounds, protection groups are used extensively. Protection groups are used to mask specific functionality which then allows other transformations to be effected in the molecule. After the intended transformation is carried out, the protected functionality is then regenerated by removal of the protecting group. The hydroxyl functionality has been found to be effectively protected by transformation to the silyl ether by reaction with alkyl chloro silanes.

Alkyl chloro silanes have been prepared by several methods. One method involves reaction of an alkyllithium with a dialkyl dichloro silane as illustrated below:

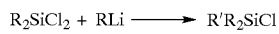

$$R_2SiCl_2 + RLi \longrightarrow R'R_2SiCl$$

* Lithium Specific Plant Equipment
* Ability to Handle Pyrophoric Materials on Plant Scale The resulting product is the trialkyl chloro silane. Preparation of alkyllithium requires access to lithium industry specific plant equipment and knowledge of handing pyrophric materials on plant scale. See U.S. Pat. No. 5,332,853 to Morrison et al.

Many preparations of alkyl chloro silanes involve chlorination of a trialkyl silane or trialkyl silanol in the last step, as illustrated below:

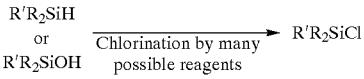

Varied starting materials ⟶

R'R$_2$SiH
or      Chlorination by many   ⟶ R'R$_2$SiCl
R'R$_2$SiOH   possible reagents

* Many Steps
* Cost Prohibited

Unfortunately, preparation of the starting trialkyl silane or trialkyl silanol usually requires several steps and is hence economically unfavorable. See, for example, JP 62022790, JP 60222492, JP 08291180, JP 08119978, EP 652,221, EP 556,802, EP 557,762, JP 06247987, JP 06128274. See also EP 298,487 and U.S. Pat. No. 5,312,949. See also EP 278,368.

Another preparation of alkyl chloro silanes involves reaction of an alkyl magnesium halide with a dialkyl dichloro silane in the present of a catalyst, as illustrated below:

$$R_2SiX_2 + R'MgX \longrightarrow R'R_2SiX + MgX_2$$

* Use of Toxic Catalyst

The catalyst of choice to effect reaction is Cu(I)CN. See, for example, JP 0831183, JP 08333374. See also EP 656,363, EP 405,560, and U.S. Pat. No. 4,650,891. Due to the highly toxic nature of Cu(I)CN, industrial preparation of alkyl chloro silanes using an alkyl magnesium process requires experience using toxic materials on industrial scale.

SUMMARY OF THE INVENTION

The present invention provides catalyst systems useful in the production of substituted compounds, including alkyl substituted silane compounds. The catalyst systems of the invention include at least two components. A first component can be a copper (I) or (II) halide, and preferably is copper (I) or (II) chloride. At least one additional metal salt which is different from the copper halide is also present as a catalyst in the mixed catalyst system of the invention. Exemplary metal salts include Group IA, Group IIA, Group IIIA, Group IVA and transition metal salts. The anion of the metal salt can vary, but in one currently advantageous embodiment of the invention, the anion is a cyanide anion.

The mixed catalyst systems of the invention are useful in the production of substituted silanes. In this regard, the present invention also provides a process in which a silane of the formula $R_yH_zSiX_{4-y-z}$ is reacted with an alkyl magnesium halide of the formula $R^1MgX^1$, wherein each R and $R^1$ is independently selected from the group consisting of alkyl, substituted alkyl, aryl, substituted aryl, cycloalkyl and substituted cycloalkyl, each X is independently selected from the group consisting of halides and alkoxides, $X^1$ is halide, and y and z can each independently be 0, 1, 2 or 3, in the presence of a mixed catalyst system.

The present invention can provide several advantages. For example, the mixed catalyst systems can be cost effective sources of catalytic activity. Further the present invention can minimize exposure to reagents such as cyanides reagents without detrimental impact on catalytic activity. Further the mixed catalyst system can offer increased flexibility in selection of catalyst reagents.

DETAILED DESCRIPTION OF THE INVENTION

The processes of the invention for making substituted silanes include reacting a silane of the formula $R_yH_zSiX_{4-y-z}$ with an alkyl magnesium halide of the formula $R^1MgX^1$, wherein each R and $R^1$ is independently selected from the group consisting of alkyl, substituted alkyl, aryl, substituted aryl, cycloalkyl and substituted cycloalkyl, each X is independently selected from the group consisting of halides and alkoxides, $X^1$ is halide, and y and z can each independently be 0, 1, 2 or 3, in the presence of a mixed catalyst system. In particular, it has been discovered that a mixed catalyst system comprising a copper (I) or (II) halide and a Group IA, IIA, IIIA, IVA, or transition metal salt of an appropriate anion catalyzes the reaction of alkyl magnesium compounds with substituted silanes, including alkyl halo silanes.

A currently preferred copper halide is copper chloride. The metal salt includes salts of Groups IA, IIA, IIIA, and IVA metals of the Periodic Table of Elements, namely, Li, Na, K, Rb, Cs, Fr, Be, Mg, Ca, Sr, Ba, Ra, Al, Sn, Pb, as well as salts of transition metals such as Fe, Zn, Ti, and Zr, and the like. Exemplary anions useful in the metal salt of the mixed catalyst system of the invention include without limitation $Cl^-$, $F^-$, $R^3O^-$, $R^3CC^-$, $NCS^-$, $CN^-$, $X_4O^-$, $I^-$, $Br^-$, $R^3CO_2^-$, $C_2O_2^{-2}$, $CuCl_4^-$, $O^{-2}$, and $R^{3-}$, wherein each $R^3$ is independently selected from the group consisting of alkyl, substituted alkyl, cycloalkyl, substituted cycloalkyl, aryl and substituted aryl and each X is halide.

The reaction can be conducted in a polar or mixed polar/hydrocarbon solvent system, typically at a temperature from about room temperature up to reflux, although reaction temperatures can be outside of this range. Exemplary polar solvents include, but are not limited to, diethyl ether, dibutyl ether, tetrahydrofuran, 2-methyltetrahydrofuran, methyl tert-butyl ether, and the like, and mixtures thereof. Exemplary hydrocarbon solvents include, but are not limited to, inert liquid alkanes, cycloalkanes and aromatic solvents, and mixtures thereof. Exemplary alkanes and cycloalkanes include those containing five to 10 carbon atoms, such as pentane, hexane, cyclohexane, methylcyclohexane, heptane, methylcycloheptane, octane, decane and the like and mixtures thereof. Exemplary aromatic solvents include those containing six to ten carbon atoms, such as toluene, ethylbenzene, p-xylene, m-xylene, o-xylene, n-propylbenzene, isopropylbenzene, n-butylbenzene, and the like and mixtures thereof. A currently preferred solvent is tetrahydrofuran (THF). Each catalyst is present in an amount ranging from about 0.01 to about 15 mole percent, and preferably from about 0.1 to about 1 mole percent.

As used herein, the term "alkyl" refers to straight chain and branched C1–C25 alkyl. The term "substituted alkyl" refers to C1–C25 alkyl substituted with one or more lower C1–C10 alkyl, lower alkoxy, lower alkylthio, or lower dialkylamino. The term "cycloalkyl" refers to C3–C12 cycloalkyl. The term "substituted cycloalkyl" refers to C3–C12 cycloalkyl substituted with one or more lower C1–C10 alkyl, lower alkoxy, lower alkylthio, or lower dialkylamino. The term "aryl" refers to C5–C25 aryl having one or more aromatic rings, each of 5 or 6 carbon atoms. Multiple aryl rings may be fused, as in naphthyl or unfused, as in biphenyl. The term "substituted aryl" refers to C5–C25 aryl substituted with one or more lower C1–C10 alkyl, lower alkoxy, lower alkylthio, or lower dialkylamino. Exemplary aryl and substituted aryl groups include, for example, phenyl, benzyl, and the like.

The current invention has been shown to be particularly useful in the preparation of t-butyl dimethyl silyl chloride, a chloro silane which is commonly used on industrial scale in the pharmaceutical industry. Reaction of t-butyl magnesium chloride with dichlorodimethylsilane resulted in t-butyl dimethyl silyl chloride (TBSCl) preparation in 90% yield using the current invention. This result was obtained employing the mixed catalyst of Cu(I)Cl and KCN as the metal salt. No product formation is observed in the absence of a catalyst. Typical results obtained employing Cu(I)Cl (alone) are 20–30% yield.

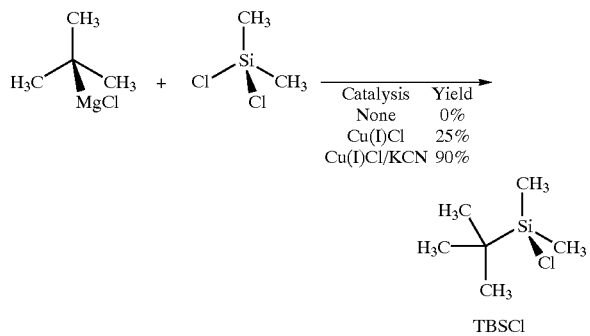

In addition to above mixed catalysis, other solvent additives can be added to help solubilize the slightly insoluble copper cation. Such additives or modifiers are known in the art and include without limitation trialkyl amines, tetramethylethylenediamine (TMEDA), diethylenetriamine, triethylene tetraamine and N-alkyl capped derivatives thereof, and the like as well as mixtures thereof.

Other modifiers can also be added to solubilize and more importantly disassociate the row IA, IIA, IIIA, IVA or transition metal from its anion. These modifiers include without limitation crown ethers such as 18-crown-6, 12-crown-4, and their substituted derivatives, cryptand complexing agents, and various glymes such as monoglyme, ethyl glyme, diglyme, ethyl diglyme, triglyme, butyl diglyme, tretraglyme, and polyglyme, and the like and mixtures thereof.

The current invention is a very cost effective source of catalytic activity. If addition of a single copper salt or single entity, in which the appropriate catalytic anion desired is already present as the counter ion on copper, were added as a single compound, the single entity catalysis would be more expensive to prepare. For instance, if the use of copper (I) cation in the present of phenyl acetylide anion were desired, one would have to prepare copper (I) phenyl acetylide from an appropriate copper derivative and lithium or sodium phenyl acetylide which would be cost ineffective. In addition to the cost of preparing a single entity catalysis, double handling of a toxic anions such as CN⁻ would certainly be disadvantaged.

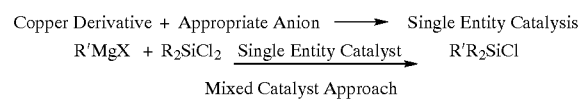

* Cheaper Catalyst System
* Less handing of Potentially Toxic Reagents

The current invention also allows infinite flexibility of the catalyst system which is not available from the single entity approach. It has been speculated by some authors that in copper systems, the anion adds to the silyl derivative to form a pentacoordinated silicon atom which is then more susceptible to nucleophilic attach by alkyl magnesium compounds. Patrick Lennon, David Mack, Quentin Thompson, *Organometallics,* 1989, 8, 1122; Robert Corriu, Christian Guerin, Bernard Henner, W. W. C. Wong Man, *Organometallics,* 1988, 7, 237. Copper cations can also exchange with alkyl magnesium compounds to form alkyl copper derivatives. H. O. House, W. L. Respess, G. M. Whitesides, *J. Org. Chem.,* 1966, 31, 3128. Both of the above potential catalytic activities could effect reaction in combination. Therefore, when making use of a single entity approach, one does not have the flexibility of varying the ratios of copper to the catalytic anion, which would be important if the catalysis regeneration rate were different for each of the two species. While employing the mixed catalysis system, use of the two catalytic agents can be varied to account for a difference in catalyst regeneration rate. The current invention's reagent flexibility would also be of advantage to reduce the quantity of toxic catalytic species, such as CN⁻ used as the catalytic anion, when carrying out these transformations on industrial scale given the appropriate catalysis regeneration rates for the given species.

The present invention is described above as useful in the production of substituted silanes. However, the mixed catalyst systems of the invention may be useful in substitution, or alkylation, reactions of metal or metalloid substrates generally (in addition to alkoxy silanes or halosilanes), including alkyl-halogen exchange reactions involving halogen or alkoxy containing Group IVA or Group VA compounds. For example, the mixed catalyst system of the invention may also be useful in the production of organo-silicone compounds, organotin compounds, alkyl or aryl phosphines, and the like. Thus the catalyst systems of the invention can be used to alkylate compounds of the formula $R_yH_zAX_{4-y-z}$ or $R_yH_zBX_{3-y-z}$, in which R, H, X, y and z are the same as defined above, A is an element from Group IVA of the Periodic Table of Elements, including silicon, carbon, germanium, and tin, and B is an element from Group VA of the Periodic Table of Elements, including phosphorous.

The mixed catalyst systems of the invention can also be useful in substitution reactions involving a halogen or alkoxy containing transition metal reagent, such as those used in the production of ligands, metallocene catalysts (in which a hydrocarbon such as a cyclopentadienide is reacted with a transition metal halide) and the like.

The mixed catalyst systems are particularly useful for alkylation processes in which a bulky or highly hindered substituent, such as a tertiary hydrocarbyl group, is added to a halogen containing Group IVA or Group VA compound or transition metal halide. Tertiary hydrocarbyl groups include without limitation tertiary alkyl groups such as tert-butyl, 1,1-dimethylpropyl, and 1,1-diethylpropyl, and aryl-group containing tert-alkyl groups, such as 1,1-dimethylbenzyl. Other bulky groups include isopropyl, 2-ethylhexyl, n-octyl, and the like.

Exemplary organosilanes include without limitation t-butyldimethylchlorosilane, t-butylsilane, t-butyltrichlorosilane, di-(t-butyl)dichlorosilane, di-(t-butyl)methylchlorosilane, di-(t-butylsilane), t-butyldiphenylsilane, t-butyldiphenylchlorosilane, triisopropylsilane, triisopropylchlorosilane, and the like and mixtures thereof.

Exemplary organogermanes include without limitation t-butyldimethylchlorogermane, t-butylgermane, t-butyltrichlorogermane, di-(t-butyl)dichlorogermane, di-(t-butyl)methylchlorogermane, di-(t-butylgermane), t-butyldiphenylgermane, t-butyldiphenylchlorogermane, triisopropylgermane, triisopropylchlorogermane, and the like and mixtures thereof.

Exemplary organotins include without limitation t-butyldimethylchlorotin, t-butyldimethyltin, t-butyldiphenyltin, t-butyldiphenylchlorotin, di-(t-butyl)-dichlorotin, triphenylchlorotin, tri-n-octyltin, and the like and mixtures thereof.

Exemplary phosphines include without limitation tri-(isopropyl)phosphine, tri-(t-butyl)phosphine, tri-(1-naphthyl)phosphine, di-(t-butyl)chlorophosphine, di-(t-butyl)phosphine, di-(isobutyl)phosphine, and the like and mixtures thereof.

The following examples serve to illustrate the invention but are not intended to be limitations thereon.

EXAMPLE 1

Use of Cu(I)CN as a Catalyst

To a 125 ml 3 neck flask fitted with a condenser and thermocouple under argon was added 15 ml THF. To this solution was added 0.042 g (0.4683 mmoles) copper (I) cyanide followed by addition of 6.04 g (0.0468 moles) dimethyldichloro silane. To this mixture held at 25° C. was added dropwise 30 ml of a 19wt % (0.0468 moles) solution of t-butyl magnesium chloride in THF over 20 minutes. After addition was complete heated reaction to 60° C. for 4 hr. Reaction mixture was then cooled to 25° C. followed by addition of 25 ml of heptane. Solid magnesium chloride which precipitated out of the reaction mixture was then removed by filtration. The resulting solution contained 6.35 g of t-butyldimethyl chloro silane (90% yield) with only trace quantities of other identifiable impurities.

EXAMPLE 2

Use of Cu(I)Cl as a Catalyst

To a 125 ml 3 neck flask fitted with a condenser and thermocouple under argon was added 15 ml THF. To this solution was added 0.042 g (0.4683 mmoles) copper (I) chloride followed by addition of 6.04 g (0.0468 moles) dimethyldichloro silane. To this mixture held at 25° C. was added dropwise 30 ml of a 19wt % (0.0468 moles) solution of t-butyl magnesium chloride in THF over 20 minutes. After addition was complete heated reaction to 60° C. for 4 hr. Reaction mixture was then cooled to 25° C. followed by addition of 25 ml of heptane. Solid magnesium chloride which precipitated out of the reaction mixture was then removed by filtration. The resulting solution contained 1.764 g of t-butyldimethyl chloro silane (25% yield) along with other higher boilers.

EXAMPLE 3

Use of Cu(I)Cl and KCN as a Mixed Catalyst

To a 125 ml 3 neck flask fitted with a condenser and thermocouple under argon was added 15 ml THF. To this solution was added 0.042 g (0.4683 mmoles) copper (I) chloride and 0.030 g (0.4683 mmoles) potassium cyanide followed by addition of 6.04 g (0.0468 moles) dimethyldichloro silane. To this mixture held at 25° C. was added dropwise 30 ml of a 19 wt % (0.0468 moles) solution of t-butyl magnesium chloride in THF over 20 minutes. After addition was complete heated reaction to 60° C. for 4 hr. Reaction mixture was then cooled to 25° C. followed by addition of 25 ml of heptane. Solid magnesium chloride which precipitated out of the reaction mixture was then removed by filtration. The resulting solution contained 6.42 g of t-butyldimethyl chloro silane (91% yield) with only trace quantities of other identifiable impurities.

EXAMPLE 4

Use of Cu(I)Cl and KCN as a Mixed Catalyst in the Present of 18-crown-6

To a 125 ml 3 neck flask fitted with a condenser and thermocouple under argon is added 15 ml THF. To this solution is added 0.042 g (0.4683 mmoles) copper (I) chloride, 0.030 g (0.4683 mmoles) potassium cyanide and 0.0132 g (0.05mmoles) 18-crown-6 followed by addition of 6.04 g (0.0468 moles) dimethyldichloro silane. To this mixture held at 25° C. is added dropwise 30 ml. of a 19 wt % (0.0468 moles) solution of t-butyl magnesium chloride in THF over 20 minutes. After addition is complete, the reaction mixture is heated to 60° C. for 4 hr. Reaction mixture is then cooled to 25° C. followed by addition of 25 ml. of heptane. Solid magnesium chloride, which precipitates out of the reaction mixture, is then removed by filtration. The resulting solution contains t-butyldimethyl chloro silane with only trace quantities of other identifiable impurities.

EXAMPLE 5

Use of Cu(I)Br and Lithium Phenyl Acetylide as a Mixed Catalyst

To a 125 ml 3 neck flask fitted with a condenser and thermocouple under argon is added 15 ml THF. To this solution is added 0.067 g (0.4683 mmoles) copper (1) bromide and 0.051 g (0.4683 mmoles) lithium phenyl acetylide followed by addition of 6.04 g (0.0468 moles) dimethyldichloro silane. To this mixture held at 25° C. is added dropwise 30 ml. of a 19 wt. % (0.0468 moles) solution of t-butyl magnesium chloride in THF over 20 minutes. After addition is complete, the reaction mixture is heated to 60° C. for 4 hr. Reaction mixture is then cooled to 25° C. followed by addition of 25 ml. of heptane. Solid magnesium chloride, which precipitates out of the reaction mixture, is then removed by filtration. The resulting solution contains t-butyldimethyl chloro silane with only trace quantities of other identifiable impurities.

EXAMPLE 6

Use of Cu(I)Br and Sodium Thiocyanate as a Mixed Catalyst

To a 125 ml 3 neck flask fitted with a condenser and thermocouple under argon is added 15 ml THF. To this solution is added 0.067 g (0.4683 mmoles) copper (I) bromide and 0.038 g (0.4683 mmoles) sodium thiocyanate followed by addition of 6.04 g (0.0468 moles) dimethyldichloro silane. To this mixture held at 25° C. is added dropwise 30 ml. of a 19 wt. % (0.0468 moles) solution of t-butyl magnesium chloride in THF over 20 minutes. After addition is complete, the reaction mixture is heated to 60° C. for 4 hr. Reaction mixture is then cooled to 25° C. followed by addition of 25 ml. of heptane. Solid magnesium chloride, which precipitates out of the reaction mixture, is then removed by filtration. The resulting solution contains t-butyldimethyl chloro silane with only trace quantities of other identifiable impurities.

The foregoing examples are illustrative of the present invention and are not to be construed as limiting thereof. Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A process for making substituted silanes, comprising reacting a silane of the formula $R_yH_zSiX_{4-y-z}$ with an alkyl magnesium halide of the formula $R^1MgX^1$, wherein each R and $R^1$ is independently selected from the group consisting of alkyl, substituted alkyl, aryl, substituted aryl, cycloalkyl and substituted cycloalkyl, each X is independently selected from the group consisting of halides and alkoxides, $X^1$ is halide, and y and z each independently can be 0, 1, 2 or 3, in the presence of a mixed catalyst system.

2. The process of claim 1, wherein said mixed catalyst system comprises:
   (1) at least one copper halide; and
   (2) at least one salt selected from the group consisting of salts of a Group IA element of the Periodic Table of Elements, salts of a IIA element of the Periodic Table of Elements, salts of a transition metal, salts of a IIIA element of the Periodic Table of Elements, salts of a IVA element of the Periodic Table of Elements and mixtures thereof.

3. The process of claim 2, wherein said at least one copper halide is copper (I) halide or copper (II) halide.

4. The process of claim 3, wherein said at least one copper halide is copper (I) chloride or copper (II) chloride.

5. The process of claim 2, wherein said at least one salt is a salt of a Group IA element.

6. The process of claim 2, wherein said at least one salt is a salt of a Group IIA element.

7. The process of claim 2, wherein said at least one salt is a salt of a transition metal selected from the group consisting of Fe, Zn, Ti, and Zr.

8. The process of claim 2, wherein said at least one salt is a salt of a Group IIIA element.

9. The process of claim 2, wherein said at least one salt is a salt of a Group IVA element.

10. The process of claim 2, wherein said at least one salt comprises an anion selected from the group consisting of $Cl^-$, $F^-$, $R^3O^-$, $R^3CC^-$, $NCS^-$, $CN^-$, $X_4O^-$, $I^-$, $Br^-$, $R^3CO_2^-$, $C_2O_2^{-2}$, $CuCl_4^-$, $O^{-2}$, and $R^{3-}$, wherein each $R^3$ is independently selected from the group consisting of alkyl, substituted alkyl, cycloalkyl, substituted cycloalkyl, aryl and substituted aryl and each X is halide.

11. The process of claim 1, wherein said anion is $CN^-$.

12. The process of claim 1, wherein said process is conducted in a polar solvent.

13. The process of claim 12, wherein said polar solvent is selected from the group consisting of tetrahydrofuran, ethyl ether, diethyl ether, dibutyl ether, 2-methyltetrahydrofuran, methyl tert-butyl ether, and mixtures thereof.

14. The process of claim 12, wherein said solvent further comprises a modifier selected from the group consisting of trialkyl amines, tetramethylethylenediamine (TMEDA), diethylenetriamine, triethylene tetraamine, N alkyl capped derivatives thereof and mixtures thereof.

15. The process of claim 12, wherein said solvent further comprises a modifier selected from the group consisting of 18-crown-6, 12-crown-4, and their substituted derivatives, cryptand complexing agents, and glymes.

16. A process for making substituted silanes, comprising reacting a silane of the formula $R_yH_zSiX_{4-y-z}$ with an alkyl magnesium halide of the formula $R^1MgX^1$, wherein each R and $R^1$ is independently selected from the group consisting of alkyl, substituted alkyl, aryl, substituted aryl, cycloalkyl and substituted cycloalkyl, each X is independently selected from the group consisting of halides and alkoxides, $X^1$ is halide, and y and z each can independently be 0, 1, 2 or 3, in the presence of a mixed catalyst system comprising copper halide and at least one cyanide.

17. The process of claim 16, wherein said at least one cyanide is selected from the group consisting of Group IA cyanides, Group IIA cyanides, Group IIIA cyanides, Group IVA cyanides, and transition metal cyanides.

18. The process of claim 17, wherein said at least one cyanide is a Group IA metal cyanide.

19. A process for making t-butyl dimethyl chlorosilane comprising reacting t-butyl magnesium chloride and dichlorodimethylsilane in the presence of a mixed catalyst system comprising copper chloride and potassium cyanide.

20. A mixed catalyst system comprising:
   (1) at least one copper halide; and
   (2) at least one salt selected from the group consisting of salts of a Group IA element of the Periodic Table of Elements, a Group IIA element of the Periodic Table of Elements, salts of a transition metal selected from the group consisting of Fe, Zn, Ti, and Zr, a Group IIIA element of the Periodic Table of Elements, a Group IVA element of the Periodic Table of Elements and mixtures thereof.

21. The mixed catalyst system of claim 20, wherein said at least one copper halide is copper (I) halide or copper (II) halide.

22. The mixed catalyst system of claim 20, wherein said at least one copper halide is copper (I) chloride or copper (II) chloride.

23. The mixed catalyst system of claim 20, wherein said at least one salt is a salt of a Group IA element.

24. The mixed catalyst system of claim 20, wherein said at least one salt is a salt of a Group IIA element.

25. The mixed catalyst system of claim 20, wherein said at least one salt is a salt of a Group IIIA element.

26. The mixed catalyst system of claim 20, wherein said at least one salt is a salt of a Group IVA element.

27. The mixed catalyst system of claim 20, wherein said at least one salt comprises an anion selected from the group consisting of $Cl^-$, $F^-$, $R^3O^-$, $R^3CC^-$, $NCS^-$, $CN^-$, $X_4O^-$, $I^-$, $Br^-$, $R^3CO_2^-$, $C_2O_2^{-2}$, $CuCl_4^-$, $O^{-2}$, and $R^{3-}$, wherein each $R^3$ is independently selected from the group consisting of alkyl, substituted alkyl, cycloalkyl, substituted cycloalkyl, aryl and substituted aryl and each X is halide.

28. The mixed catalyst system of claim 27, wherein said anion is $CN^-$.

29. An alkylation process, comprising reacting a halogen or alkoxy substituted metal or metalloid substrate with an alkyl magnesium halide in the presence of a mixed catalyst system, wherein said mixed catalyst system comprises at least one copper halide and at least one additional salt which is different from said copper halide.

30. The process of claim 29, wherein said mixed catalyst system comprises:
(1) at least one copper halide; and
(2) at least one salt selected from the group consisting of salts of a Group IA element of the Periodic Table of Elements, salts of a IIA element of the Periodic Table of Elements, salts of a transition metal, salts of a IIIA element of the Periodic Table of Elements, salts of a IVA element of the Periodic Table of Elements and mixtures thereof.

31. The process of claim 30, wherein said at least one copper halide is copper (I) chloride or copper (II) chloride.

32. The process of claim 30, wherein said at least one salt comprises an anion selected from the group consisting of $Cl^-$, $F^-$, $R^3O^-$, $R^3CC^-$, $NCS^-$, $CN^-$, $X_4O^-$, $I^-$, $Br^-$, $R^3CO_2^-$, $C_2O_2^{-2}$, $CuCl_4^-$, $O^{-2}$ and $R^{3-}$, wherein each $R^3$ is independently selected from the group consisting of alkyl, substituted alkyl, cycloalkyl, substituted cycloalkyl, aryl and substituted aryl and each X is halide.

33. The process of claim 32, wherein said anion is $CN^-$.

34. A process for alkylating a halogen or alkoxy substituted metalloid substrate, comprising reacting a compound of the formula $R_yH_zAX_{4-y-z}$ or $R_yH_zBX_{3-y-z}$ with an alkyl magnesium halide of the formula $R^1MgX^1$, wherein each R and $R^1$ is independently selected from the group consisting of alkyl, substituted alkyl, aryl, substituted aryl, cycloalkyl and substituted cycloalkyl, each X is independently selected from the group consisting of halides and alkoxides, $X^1$ is halide, y and z are each independently 0, 1, 2 or 3, A is an element selected form Group IVA of the Periodic Table of Elements, and B is an element selected from Group VA of the Periodic Table of Elements, in the presence of a mixed catalyst system, said mixed catalyst system comprising copper halide and at least one additional salt which is different from said copper halide.

35. The process of claim 34, wherein said mixed catalyst system comprises:
(1) at least one copper halide; and
(2) at least one salt selected from the group consisting of salts of a Group IA element of the Periodic Table of Elements, a Group IIA element of the Periodic Table of Elements, salts of a transition metal, a Group IIIA element of the Periodic Table of Elements, a Group IVA element of the Periodic Table of Elements and mixtures thereof.

36. The process of claim 35, wherein said at least one copper halide is copper (I) chloride or copper (II) chloride.

37. The process of claim 35, wherein said at least one salt comprises an anion selected from the group consisting of $Cl^-$, $F^-$, $R^3O^-$, $R^3CC^-$, $NCS^-$, $CN^-$, $X_4O^-$, $I^-$, $Br^-$, $R^3CO_2^-$, $C_2O_2^{-2}$, $CuCl_4^-$, $O^{-2}$, and $R^{3-}$, wherein each $R^3$ is independently selected from the group consisting of alkyl, substituted alkyl, cycloalkyl, substituted cycloalkyl, aryl and substituted aryl and each X is halide.

38. The process of claim 37, wherein said anion is $CN^-$.

39. The process of claim 4, wherein said at least one salt comprises potassium cyanide.

40. The process of claim 18, wherein said at least one cyanide comprises potassium cyanide.

41. The mixed catalyst system of claim 22, wherein said at least one salt comprises potassium cyanide.

42. The process of claim 31, wherein said at least one salt comprises potassium cyanide.

43. The process of claim 36, wherein said at least one salt comprises potassium cyanide.

44. A mixed catalyst system comprising:
(1) at least one copper halide; and
(2) at least one cyanide selected from the group consisting of Group IA cyanides, Group IIA cyanides, Group IIIA cyanides, Group IVA cyanides, and transition metal cyanides.

45. The mixed catalyst system of claim 44, wherein said at least one cyanide is a Group IA metal cyanide.

* * * * *